United States Patent [19]
Garritsen et al.

[11] 3,931,292
[45] Jan. 6, 1976

[54] PREPARATION OF OMEGA-AMINO-SUBSTITUTED BETA-ALKOXYCARBOXYLIC ESTERS

[75] Inventors: Johan W. Garritsen, Sittard; Josef M. Penders, Maastricht, both of Netherlands

[73] Assignee: Stamicarbon B.V., Geleen, Netherlands

[22] Filed: Dec. 5, 1973

[21] Appl. No.: 422,008

[30] Foreign Application Priority Data
Dec. 8, 1972  Netherlands............................ 16661

[52] U.S. Cl....... 260/482 R; 260/239.3 A; 260/404; 260/464; 260/465.4; 260/468 J
[51] Int. Cl.²......................................... C07C 101/18
[58] Field of Search............. 260/482 R, 468 J, 404

[56] References Cited
UNITED STATES PATENTS

| | | | |
|---|---|---|---|
| 3,062,884 | 11/1962 | Green .......................... | 260/570.8 R |
| 3,104,201 | 9/1963 | Testa et al. ..................... | 260/482 R |
| 3,166,562 | 1/1965 | Leditschke et al........... | 260/570.8 R |

OTHER PUBLICATIONS

Ed. F. Degering, An Outline of Organic Nitrogen Cmpds., University Lithoprinters, Ypsilanti, Mich. 1950, p. 509.

Primary Examiner—Lorraine A. Weinberger
Assistant Examiner—Paul J. Killos
Attorney, Agent, or Firm—Cushman, Darby & Cushman

[57] ABSTRACT

An omega-amino-beta-alkoxycarboxylic acid ester is prepared by subjecting to hydrogenation in the liquid phase an omega-cyano-beta-alkoxycarboxylic acid ester. The hydrogenation may be carried out at a temperature of 70° to 150°C. The amino-esters obtained can be cyclized through heating into beta-alkoxy-omega-lactams which may be applied for preparation of polyamides and copolyamides.

2 Claims, No Drawings

PREPARATION OF OMEGA-AMINO-SUBSTITUTED BETA-ALKOXYCARBOXYLIC ESTERS

This invention relates to β-alkoxycarboxylic esters and to processes for preparing such esters.

The preparation of ω-cyano-β-alkoxycarboxylic esters by reaction of an ω-cyano-acetal and a ketene is described in U.S. Pat. application Ser. No. 396,665, filed Sept. 13, 1973, which is hereby incorporated by reference. The compounds thereby obtained may be represented by the general formula

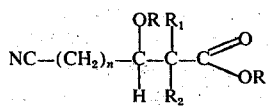

in which $n$ is an integer of from 1 to 5, the two R groups, which may be the same or different, represent an alkyl group or a cyclo-alkyl group containing not more than 10 carbon atoms, and $R_1$ and $R_2$, which may be the same or different, represent hydrogen or an alkyl group or a cyclo-alkyl group containing not more than 10 carbon atoms.

It has now been found that such ω-cyano-β-alkoxycarboxylic acid esters can be converted in good yields into the corresponding ω-amino-β-alkoxycarboxylic esters, which are new compounds.

The invention provides an ω-amino-β-alkoxycarboxylic acid ester of the general formula

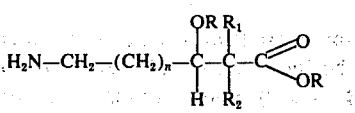

wherein
$n$ is an integer of from 1 to 5, the two R groups, which may be the same or different, represent an alkyl group or a cycloalkyl group containing not more than 10 carbon atoms, and $R_1$ and $R_2$ which may be the same or different, represent hydrogen, an alkyl group or a cycloalkyl group containing not more than 10 carbon atoms.

A particular class of amino-esters according to the invention is according to the said general formula wherein n is 2 or 3, R represents a methyl group or an ethyl group, and $R_1$ and $R_2$ represent hydrogen.

The amino-esters according to the invention have the property of being capable of cyclization by heating into β-alkoxy-ω-lactams, in which no substantial cyclization between the aminogroup and the carbon atom to which the alkoxy-group is bound occurs. Such lactams may be used for preparation of polyamides and copolyamides.

The invention also provides a process for preparing ω-amino substituted β-alkoxycarboxylic acid esters, comprising hydrogenating in the liquid phase an ω-cyano-β-alkoxycarboxylic acid ester of the general formula

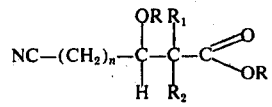

in which
$n$ is integer of from 1 to 5, the two R-groups, which may be the same or different, represent an alkyl group or a cycloalkyl group containing not more than 10 carbon atoms, and $R_1$ and $R_2$ which may be the same or different, represent hydrogen, an alkyl group or a cycloalkyl group containing not more than 10 carbon atoms.

In the process according to the invention the cyano group is hydrogenated, but no substantial hydrogenation of the alkoxy group takes place. This is surprising as hydrogenation of the alkoxy group could be expected by analogy with the hydrogenation of alkoxy ketones (see U.S. Pat. Spec. Nos. 3,065,237 and 2,676,176).

In the process according to the invention the preferred starting material is a cyano-ester according to the said general formula in which $n$ is 2 or 3, R represents a methyl group or an ethyl group, the two R groups are identical, and $R_1$ and $R_2$ represent hydrogen. Such cyano-esters can be prepared by reaction of ketene with the acetal of β-cyanopropionaldehyde or γ-cyanobutyraldehyde respectively, and methyl alcohol or ethyl alcohol.

The hydrogenation reaction according to the invention may be carried out at temperatures of from 70° to 150°C, to achieve a high efficiency with a rapid reaction.

Hydrogen used in the hydrogenation reaction may be for instance from 10 to 100 atmospheres. The pressure used however should be such that the reaction is effected in the liquid phase at the particular temperature used. The hydrogenation is preferably effected in the presence of ammonia, whereby the formation of secondary and tertiary amines is inhibited.

In the process according to the invention various hydrogenation catalysts may be applied, for example Raney-nickel, Raney-cobalt, platinum or palladium.

The hydrogenation according to the invention may be carried out in a solvent, for example water, dioxane, ethyl acetate, cyclohexane, methyl cyclohexane, ethanol or methanol, the solvent may be recovered e.g. by distillation, after the reaction has ended.

If during subsequent processing the amino-ester obtained according to the invention is cyclized in the liquid phase by heating into the corresponding β-alkoxy-ω-lactam, it is not necessary for the amino-ester to be separated as such from the hydrogenation mixture obtained, and the whole reaction mixture may be subjected to the cyclization conditions.

The following Examples of the invention are provided. In Examples I and II, the cyclization of the amino-ester into the corresponding beta-alkoxy-omega-lactam is demonstrated with and without separation of the aminoester as such from the hydrogenation mixture.

EXAMPLE I 20.3 g of δ-cyano-β-methoxy-butanecarboxylic methyl ester, 230 millilitres of dioxane, and 1.1 g of Raney nickel were introduced into a 500 millilitre autoclave provided with a stirrer. The autoclave was flushed with nitrogen and 21 g of liquid ammonia were added to the mixture therein, and hydrogen is introduced into the autoclave until the pressure therein reached approximately 80 atmospheres. The mixture in the autoclave was then vigorously stirred for 1 hour at about 100°C and after cooling to room temperature the autoclave was opened, the ammonia removed by evaporation, the Raney nickel filtered off, and the filtrate concentrated by evaporation. 25 g of residue were obtained which contained 19 g of ε-amino-β-methoxypentanecarboxylic acid methyl ester and 5.25 g of dioxane. The said residue did not contain any starting material. The reaction efficiency was 92%. By distillation at reduced pressure the amino-ester was obtained in a practically pure condition (boiling point 84°–86°C at 1.3 millimetres Mercury; $n^{20}_d = 1.4469$).

15 g of the ε-amino-β-methoxy-pentanecarboxylic acid methyl ester thus obtained were dissolved in 160 g of dioxane in a 500 millilitre autoclave provided with a stirrer. The autoclave was flushed with nitrogen and the solution herein heated for 1 hour at 260°–265°C, the pressure in the autoclave being about 20 atmospheres.

After cooling, the autoclave was opened and the resulting reaction mixture concentrated by evaporation. 15 g of reaction product were obtained, containing 11% by weight of non-converted starting material and 60% by weight of β-methoxy-ε-caprolactam, corresponding to a conversion of 89% and an efficiency of 83% based on the product converted.

EXAMPLE II 20.1 g of δ-cyano-β-methoxy-butanecarboxylic acid methyl ester, 240 millilitres of dioxane and 1 g of Raney nickel were introduced into a 500 millilitre autoclave provided with a stirrer. The autoclave was flushed with nitrogen and 28 g of liquid ammonia added and hydrogen introduced into the autoclave to provide a pressure therein of 80 atmospheres. The mixture was vigorously stirred for 1 hour at a temperature of approximately 90°C and the stirring continued for a further hour at a temperature of 200°C.

After cooling, the autoclave was opened and the ammonia removed by evaporation, the Raney nickel filtered off, and the filtrate concentrated by evaporation. 19 g of residue were obtained, no starting material being present and containing 3.8 g of dioxane and 13.1 g of β-methoxy-ε-caprolactam. The efficiency was 78% based on the original quantity of cyano-ester.

Through distillation of the residue at reduced pressure practically pure β-methoxy-ε-caprolactam was obtained (boiling point 166°C at 9 millimetres Mercury, melting point 54–56°C).

EXAMPLE III 13 g of ε-cyano-β-methoxy-pentanecarboxylic acid methyl ester, 240 millilitres of dioxane, 0.75 g of Raney nickel and 1.5 g of water were introduced into a 500 millilitre autoclave provided with a stirrer.

The autoclave was flushed with nitrogen and 25 g of liquid ammonia added, and hydrogen introduced into the autoclave to provide a pressure of 80 atmospheres therein. The mixture was then vigorously stirred for 1 hour at 90°C.

After cooling to room temperature the autoclave was opened and the ammonia removed by evaporation, the Raney nickel filtered off, and the filtrate concentrated by evaporation. 14.2 g of residue were thus obtained which contained 9.9 g of ω-amino-β-methoxy-hexanecarboxylic acid methyl ester and 3.5 g of dioxane. The residue did not contain any starting product. The reaction efficiency was 75%. By distillation at reduced pressure the amino-ester was obtained in a substantially pure state (boiling point 124°–125°C at 1 millimetre Mercury; $n^{20}_D = 1.4643$).

What is claimed is:

1. An ω-amino-β-alkoxycarboxylic acid ester of the general formula

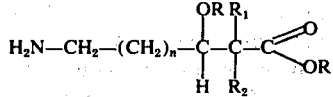

wherein n is an integer of from 1 to 5, the two R groups which may be the same or different, represent an alkyl group or a cycloalkyl group containing not more than 10 carbon atoms, and $R_1$ and $R_2$, which may be the same or different, represent hydrogen, an alkyl group or a cycloalkyl group containing not more than 10 carbon atoms.

2. An ester of the general formula of claim 1 wherein n is 2 or 3, R represents a methyl group or an ethyl group, and $R_1$ and $R_2$ represent hydrogen.

* * * * *